US012384735B2

(12) United States Patent
Shimura et al.

(10) Patent No.: US 12,384,735 B2
(45) Date of Patent: Aug. 12, 2025

(54) MANUFACTURING METHOD OF BUTADIENE

(71) Applicants: CHIYODA CORPORATION, Yokohama (JP); UBE CORPORATION, Ube (JP)

(72) Inventors: Mitsunori Shimura, Yokohama (JP); Dai Takeda, Yokohama (JP); Jun Matsumoto, Yokohama (JP); Atsushi Yamada, Yamaguchi (JP); Yuki Nagao, Yamaguchi (JP)

(73) Assignees: CHIYODA CORPORATION, Yokohama (JP); UBE CORPORATION, Yamaguchi (JP)

( * ) Notice: Subject to any disclaimer, the term of this patent is extended or adjusted under 35 U.S.C. 154(b) by 232 days.

(21) Appl. No.: 18/548,980

(22) PCT Filed: Mar. 1, 2022

(86) PCT No.: PCT/JP2022/008576
§ 371 (c)(1),
(2) Date: Sep. 5, 2023

(87) PCT Pub. No.: WO2022/190962
PCT Pub. Date: Sep. 15, 2022

(65) Prior Publication Data

US 2024/0158321 A1 May 16, 2024

(30) Foreign Application Priority Data

Mar. 9, 2021 (JP) ................................ 2021-037409

(51) Int. Cl.
*C25B 3/26* (2021.01)
*C07C 2/08* (2006.01)
(Continued)

(52) U.S. Cl.
CPC ................. *C07C 5/48* (2013.01); *C25B 1/04* (2013.01); *C25B 3/03* (2021.01); *C25B 3/26* (2021.01); *C25B 15/029* (2021.01); *C25B 15/081* (2021.01)

(58) Field of Classification Search
CPC ... C07C 5/48; C07C 2521/12; C07C 2523/31; C07C 2523/648; C07C 2523/745;
(Continued)

(56) References Cited

U.S. PATENT DOCUMENTS

| | | | | |
|---|---|---|---|---|
| 2005/0171311 | A1* | 8/2005 | Schindler | C07C 5/3335 526/335 |
| 2014/0088331 | A1* | 3/2014 | Rolland | B01J 31/0212 585/326 |
| 2020/0392632 | A1 | 12/2020 | Oh et al. | |

FOREIGN PATENT DOCUMENTS

| | | | |
|---|---|---|---|
| JP | 2004176129 | A | 6/2004 |
| JP | 2011148720 | A | 8/2011 |

(Continued)

OTHER PUBLICATIONS

International Search Report for Japanese PCT Application No. PCT/JP2022/008576 mailed Apr. 26, 2022; 2 pp.

(Continued)

*Primary Examiner* — In C Bullock
*Assistant Examiner* — Jason Y Chong
(74) *Attorney, Agent, or Firm* — Armstrong Teasdale LLP

(57) ABSTRACT

A manufacturing method of butadiene includes an electrolytic reduction process that produces ethylene and oxygen from carbon dioxide and water as a raw material by electrolytic reduction, a butene producing process that produces butene by dimerizing the ethylene produced in the electrolytic reduction process, a mixing process that prepares a mixed gas by mixing the oxygen produced in the electrolytic reduction process, the butene produced in the butene pro-
(Continued)

ducing process, and air, and a butadiene producing process that produces butadiene by heating the mixed gas and oxidatively dehydrogenating the butene, wherein carbon dioxide by-produced in the butadiene producing process is used as a portion of the raw material in the electrolytic reduction process.

8 Claims, 4 Drawing Sheets

(51) Int. Cl.

| | |
|---|---|
| ***C07C 5/48*** | (2006.01) |
| ***C25B 1/04*** | (2021.01) |
| ***C25B 3/03*** | (2021.01) |
| ***C25B 15/029*** | (2021.01) |
| ***C25B 15/08*** | (2006.01) |

(58) Field of Classification Search

CPC .......... C07C 2523/75; C07C 2523/755; C07C 2523/822; C07C 2/24; C25B 1/02; C25B 1/04; C25B 3/03; C25B 3/26; C25B 15/023; C25B 15/029; C25B 15/08; C25B 15/081

See application file for complete search history.

(56) References Cited

FOREIGN PATENT DOCUMENTS

| | | | |
|---|---|---|---|
| JP | 2014062094 | A | 4/2014 |
| JP | 2015182985 | A | 10/2015 |
| JP | 2017080738 | A | 5/2017 |
| JP | 2017080739 | A | 5/2017 |
| JP | 2019085353 | A | 6/2019 |

OTHER PUBLICATIONS

Extended European Search Report for European Patent Application No. 22766921.5 dated Feb. 18, 2025; 8 pp.

* cited by examiner air
$C_4H_8$
$O_2$
$N_2$
$CO_2$, $N_2$
$C_4H_6$
$CO_2$
$H_2O$
$C_2H_4$ 1
ethylene producing process
101
$C_4H_8$
103
$C_2H_4$
102
butene producing process
3
$C_4H_8$
52
air
53
57
4
mixing process
$O_2$
$N_2$
63
64
61
butadiene producing process
5
69
$CO_2$,$N_2$
heat exchanging process
6
55
42
69
$CO_2$,$N_2$
$N_2$
butadiene separating process
7
$C_4H_6$
74
55
carbon dioxide separating process
8
oxygen combustion device
60
59
58
$O_2$
78
77
$CO_2$
$CO_2$
79
76
80
42
electrolytic reduction process
$H_2O$
$O_2$
41
$C_2H_4$
2

MANUFACTURING METHOD OF BUTADIENE

CROSS-REFERENCE TO RELATED APPLICATION

This application is a U.S. National Phase Application of PCT/JP2022/008576, filed on Mar. 1, 2022, which claims the benefit of priority to Japanese Patent Application No. 2021-037409, filed Mar. 9, 2021. The contents of these applications are hereby expressly incorporated by reference in their entirety.

TECHNICAL FIELD

The present invention relates to a manufacturing method of butadiene.

BACKGROUND ART

In recent years, a manufacturing method of ethylene has shifted from a manufacturing method of pyrolyzing naphtha to a manufacturing method of using, as a raw material, ethane acquired from a shale gas and the like. In a case where ethane is used as a raw material, the amount of butadiene by-produced together with ethylene is reduced as compared with a case where naphtha is used as a raw material. Accordingly, there is a problem that a supply-demand gap of butadiene increases. To solve this problem, Patent Documents 1 and 2 disclose a method that produces butadiene by dimerizing ethylene to produce butene and then oxidatively dehydrogenating butene.

PRIOR ART DOCUMENT(S)

Patent Document(s)

Patent Document 1: JP2014-62094A
Patent Document 2: JP2011-148720A

SUMMARY OF THE INVENTION

Task to be Accomplished by the Invention

However, in a case where butadiene is produced by oxidatively dehydrogenating butene, there is a problem that a large amount of carbon dioxide is produced by a complete combustion reaction as a side reaction. Conventionally, the produced carbon dioxide is released into the atmosphere, but it is desirable to reduce the carbon dioxide from the viewpoint of global environmental conservation.

In view of the above background, an object of the present invention is to provide a manufacturing method of butadiene that can reduce carbon dioxide emissions.

Means to Accomplish the Task

To achieve such an object, one aspect of the present invention provides a manufacturing method of butadiene, comprising: an electrolytic reduction process (2) that produces ethylene and oxygen from carbon dioxide and water as a raw material by electrolytic reduction; a butene producing process (3) that produces butene by dimerizing the ethylene produced in the electrolytic reduction process; a mixing process (4) that prepares a mixed gas by mixing the oxygen produced in the electrolytic reduction process, the butene produced in the butene producing process, and air; and a butadiene producing process (5) that produces butadiene by heating the mixed gas and oxidatively dehydrogenating the butene, wherein carbon dioxide by-produced in the butadiene producing process is used as a portion of the raw material in the electrolytic reduction process.

According to this aspect, ethylene as a raw material of butene and oxygen required for oxidative dehydrogenation can be produced by using carbon dioxide that is generated when butadiene is produced by oxidative dehydrogenation. Thus, the emissions of carbon dioxide as a greenhouse gas can be reduced. Further, the cost of a raw material can be reduced in the manufacturing method of butadiene.

In the above aspect, preferably, the manufacturing method of butadiene comprises: a heat exchanging process (6) that cools a gas composition flowing out in the butadiene producing process and containing the butadiene and the carbon dioxide; a butadiene separating process (7) that separates the butadiene from the gas composition cooled in the heat exchanging process; and a carbon dioxide separating process (8) that separates the carbon dioxide from the gas composition from which the butadiene is separated in the butadiene separating process, wherein the carbon dioxide separated in the carbon dioxide separating process is used as the portion of the raw material in the electrolytic reduction process.

According to this aspect, carbon dioxide is concentrated and supplied to the electrolytic reduction process. Accordingly, the efficiency of the electrolytic reduction can be improved.

In the above aspect, preferably, in the heat exchanging process, the gas composition flowing out in the butadiene producing process and containing the butadiene and the carbon dioxide is cooled by exchanging heat with the gas composition from which the carbon dioxide is separated in the carbon dioxide separating process.

According to this aspect, energy efficiency can be improved.

In the above aspect, preferably, the gas composition from which the carbon dioxide is separated in the carbon dioxide separating process is mixed with the mixed gas in the mixing process after exchanging heat in the heat exchanging process with the gas composition flowing out in the butadiene producing process and containing the butadiene and the carbon dioxide.

According to this aspect, the gas composition from which carbon dioxide is separated in the carbon dioxide separating process is supplied to the butadiene producing process via the mixing process after heated in the heat exchanging process. Accordingly, the energy consumption for heating a reactor of the butadiene producing process can be reduced.

In the above aspect, preferably, the manufacturing method of butadiene comprises: measuring an oxygen concentration and a flow rate of the mixed gas in the mixing process; and controlling a flow rate of the oxygen supplied from the electrolytic reduction process to the mixing process based on the oxygen concentration and the flow rate of the mixed gas.

According to this aspect, the oxygen concentration of the mixed gas can be maintained within an appropriate range.

In the above aspect, preferably, the manufacturing method of butadiene comprises: measuring a flow rate of the carbon dioxide supplied from the butadiene producing process to the electrolytic reduction process; and controlling a potential of the electrolytic reduction in the electrolytic reduction process based on the flow rate of the carbon dioxide.

According to this aspect, the efficiency of the electrolytic reduction can be improved.

In the above aspect, preferably, the manufacturing method of butadiene further comprises an ethylene producing process (101) that produces ethylene from ethane or naphtha as a raw material, wherein the ethylene produced in the ethylene producing process is used as a portion of a raw material in the butene producing process.

According to this aspect, the supplying amount of ethylene can be increased.

In the above aspect, preferably, butene by-produced in the ethylene producing process is used in the butadiene producing process.

According to this aspect, the supplying amount of butene can be increased.

Effect of the Invention

Thus, according to the above aspects, it is possible to provide a manufacturing method of butadiene that can reduce carbon dioxide emissions.

BRIEF DESCRIPTION OF THE DRAWING(S)

MODE(S) FOR CARRYING OUT THE INVENTION

Figure 1:
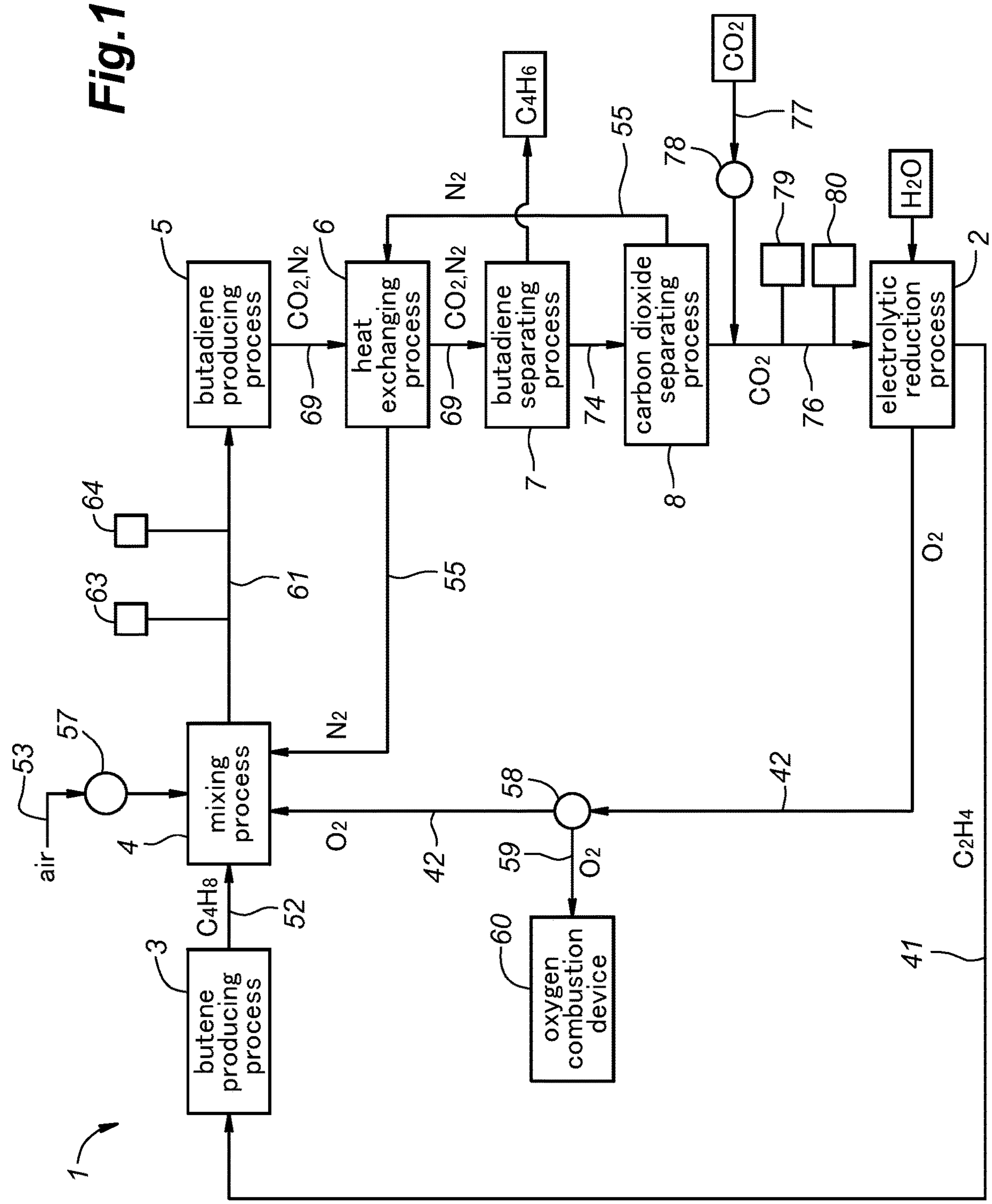
FIG. 1 is an explanatory diagram showing a butadiene manufacturing system.
Figure 2:
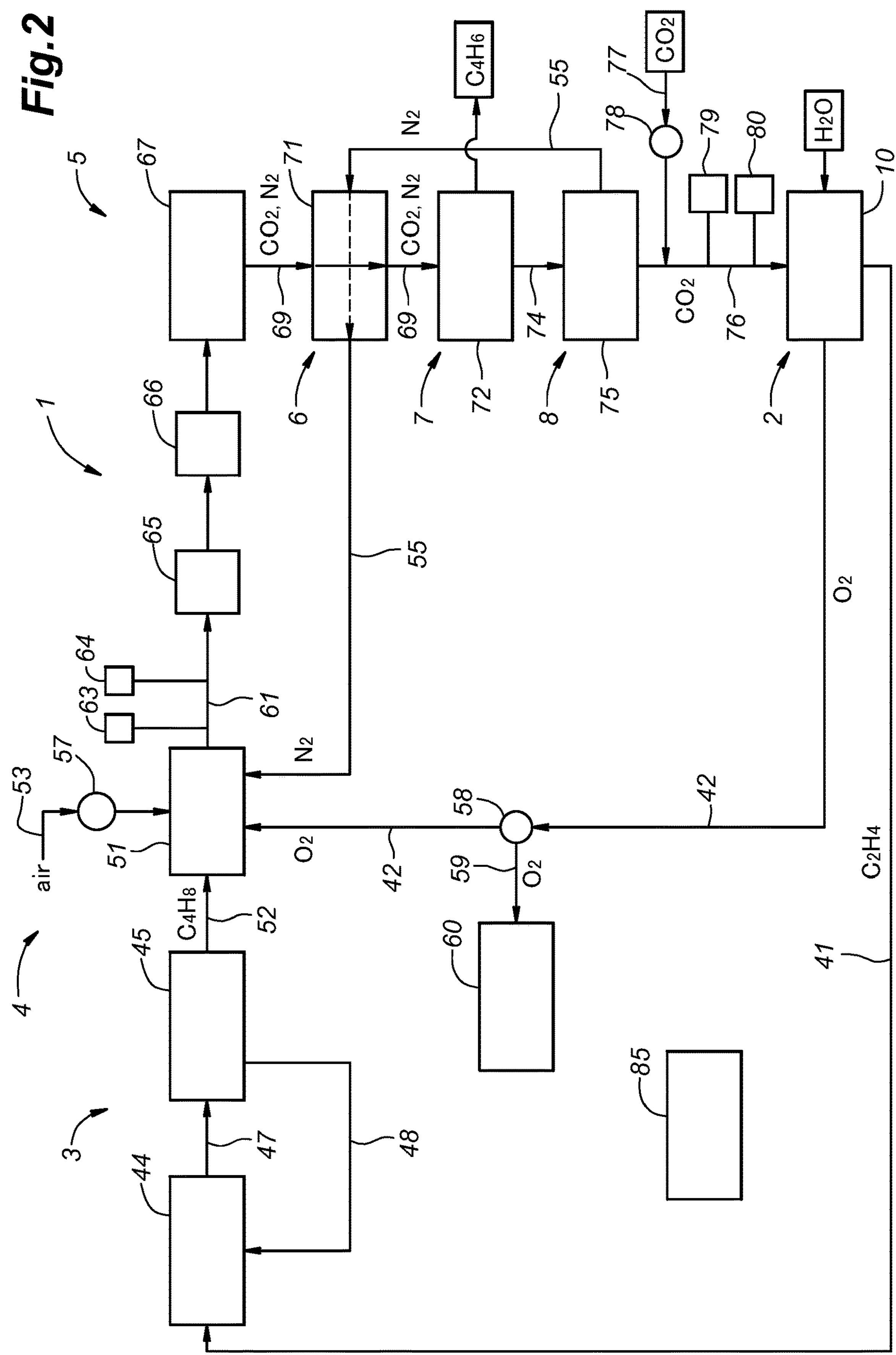
FIG. 2 is an explanatory diagram showing the butadiene manufacturing system.

In the following, an embodiment of a manufacturing method of butadiene according to the present invention will be described. As shown in FIGS. 1 and 2, a butadiene manufacturing system 1 according to the embodiment includes an electrolytic reduction process 2, a butene producing process 3, a mixing process 4, a butadiene producing process 5, a heat exchanging process 6, a butadiene separating process 7, and a carbon dioxide separating process 8.

In the electrolytic reduction process 2, ethylene and oxygen are produced from carbon dioxide and water as a raw material by electrolytic reduction.

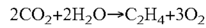

$$2CO_2+2H_2O \rightarrow C_2H_4+3O_2$$

An electrolytic reductor that uses a gas diffusion electrode for a cathode 16, an electrolytic reductor that uses a solid polymer membrane as a separator, and the like may be used for the electrolytic reduction process 2.

Figure 3:
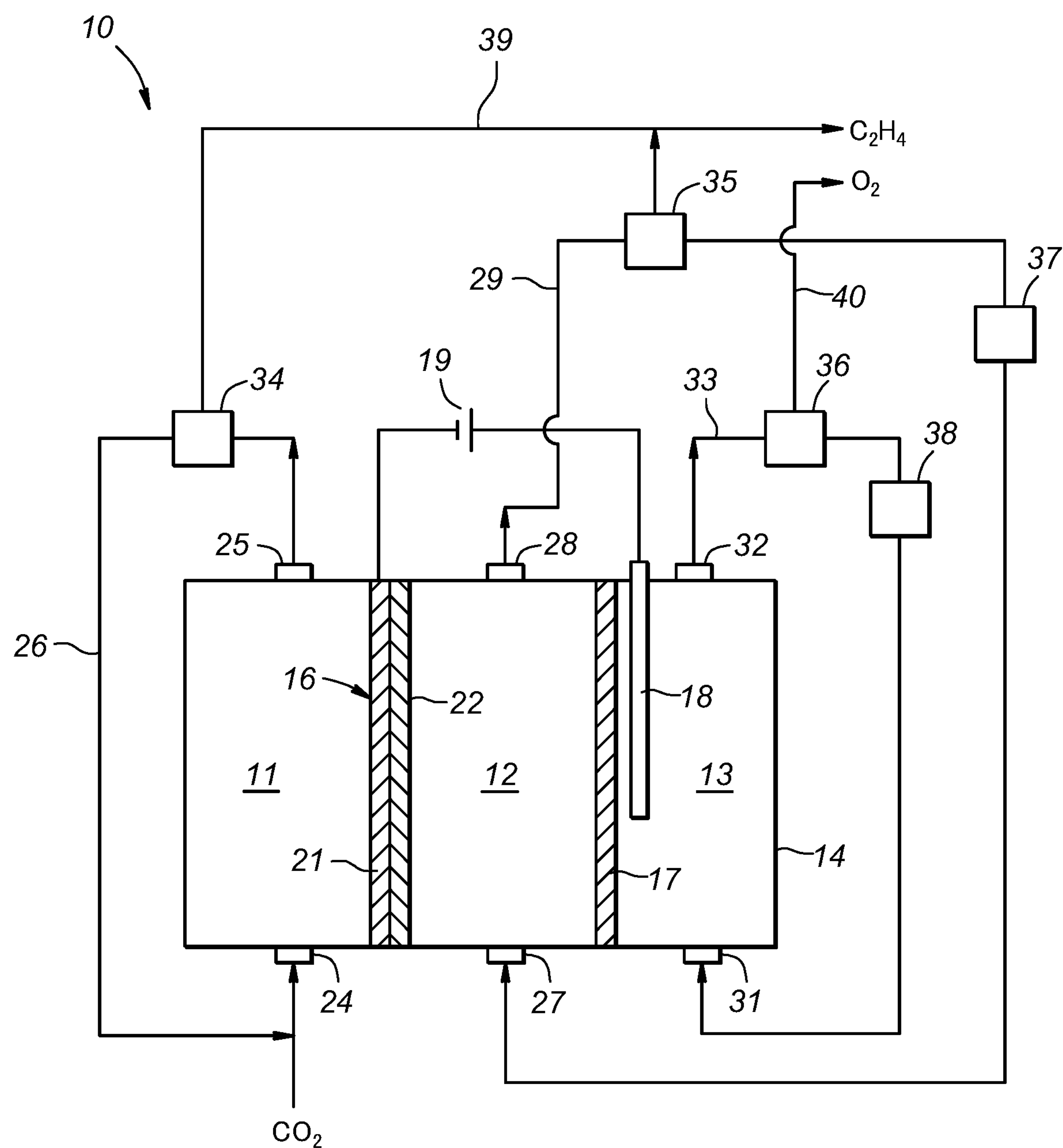
FIG. 3 is an explanatory diagram showing an electrolytic reductor.

As shown in FIG. 3, an electrolytic reductor 10 used in the electrolytic reduction process 2 may be, for example, a three-chamber electrolytic reductor. More specifically, the electrolytic reductor 10 may include an electrolytic cell 14 provided with a cathode gas chamber 11, a catholyte chamber 12, and an anolyte chamber 13 that are partitioned from each other. The cathode gas chamber 11 and the catholyte chamber 12 are partitioned by the cathode 16 as a gas diffusion electrode. The catholyte chamber 12 and the anolyte chamber 13 are partitioned by a partition wall 17 having ion conductivity. An anode 18 is arranged in the anolyte chamber 13. Gaseous carbon dioxide is supplied to the cathode gas chamber 11. Carbon dioxide is supplied from the carbon dioxide separating process 8 as described later. Catholyte is supplied to the catholyte chamber 12. Anolyte is supplied to the anolyte chamber 13. The anode 18 and the cathode 16 are connected to a DC power supply 19.

The anolyte and the catholyte are aqueous solutions in which an electrolyte is dissolved. The electrolyte includes at least one of potassium, sodium, lithium, and a compound thereof. For example, the electrolyte may include at least one selected from the group consisting of LiOH, NaOH, KOH, $Li_2CO_3$, $Na_2CO_3$, $K_2CO_3$, $LiHCO_3$, $NaHCO_3$, and $KHCO_3$.

The cathode 16 is a gas diffusion electrode, and includes a gas diffusion layer 21 and a microporous layer 22. The gas diffusion layer 21 is permeable to a gas containing carbon dioxide, but inhibits the permeation of an aqueous solution containing the catholyte. The microporous layer 22 is permeable to both the gas containing carbon dioxide and the aqueous solution containing the catholyte. The gas diffusion layer 21 and the microporous layer 22 each have a flat surface. The gas diffusion layer 21 is arranged on a side of the cathode gas chamber 11, and the microporous layer 22 is arranged on a side of the catholyte chamber 12.

For example, the gas diffusion layer 21 may be composed of a porous conductive base material such as carbon paper, carbon felt, and carbon cloth, and a water-repellent film such as polytetrafluoroethylene formed on a surface of the conductive base material. The conductive base material is connected to a negative pole of the DC power supply 19, and supplied with electrons. The microporous layer 22 is formed on a surface of the gas diffusion layer 21 by using carbon black, and the like, and carries a catalyst. The catalyst may be a known carbon dioxide reduction catalyst, and includes, for example, at least one of a Group 11 element such as copper, a Group 12 element such as zinc, a Group 13 element such as gallium, a Group 14 element such as germanium, and a metal compound thereof. The metal compound includes at least one of an oxide, a sulfide, and a phosphide. The catalyst is preferably suitable for reducing carbon dioxide to produce ethylene, and is preferably made of a material formed by combining copper or a copper compound with a metal of a Group 11 element, a Group 12 element, a Group 13 element, or a Group 14 element or a metal compound thereof, for example. A binder such as an ion exchange resin may be added to the microporous layer 22.

For example, the anode 18 consists of a metal such as titanium, nickel, molybdenum, platinum, gold, silver, copper, iron, and lead, a metal alloy thereof, a carbon-based material such as carbon, or a conductive ceramic. The anode 18 may be formed into a flat plate, a flat plate with a plurality of openings, a mesh, or a porous body. The openings of the flat plate may be formed into a circle, a rhombus, a star, and the like. The flat plate may be corrugated or curved, and a surface thereof may be uneven. The anode 18 carries an oxygen generating catalyst such as platinum or iridium. The anode 18 may be provided on a surface of the partition wall 17 on a side of the anolyte chamber 13.

The DC power supply 19 converts the electric power, which is acquired by thermal power generation, nuclear power generation, solar power generation, wind power generation, hydroelectric power generation, and the like, into direct current as necessary, and supplies the electric power to the cathode 16 and the anode 18. From the viewpoint of reducing carbon dioxide emissions, it is preferable to use, as the DC power supply 19, the electric power acquired from solar power generation, wind power generation, hydroelectric power generation, and the like that use natural energy (renewable energy). The DC power supply 19 applies a voltage such that the cathode 16 has a negative potential with respect to the anode 18. The DC power supply 19 acquires a potential of the cathode 16 by using a reference electrode, and preferably controls the voltage to be applied such that the potential of the cathode 16 is kept within a prescribed range.

The cathode gas chamber 11 includes an inlet 24 and an outlet 25. A carbon dioxide gas is supplied from the inlet 24 and discharged from the outlet 25. The outlet 25 of the cathode gas chamber 11 is connected to the inlet 24 via a gas circulation passage 26.

The catholyte chamber 12 includes an inlet 27 and an outlet 28. The inlet 27 and the outlet 28 of the catholyte chamber 12 are connected via a catholyte circulation passage 29. Similarly, the anolyte chamber 13 includes an inlet 31 and an outlet 32. The inlet 31 and the outlet 32 of the anolyte chamber 13 are connected via an anolyte circulation passage 33. The catholyte circulation passage 29 and the anolyte circulation passage 33 are provided with separators 35 and 36, respectively. The separators 35 and 36 may include a gas-liquid separator. Further, the catholyte circulation passage 29 and the anolyte circulation passage 33 may be provided with electrolyte concentration controllers 37 and 38, respectively, for adjusting electrolyte concentrations of the catholyte and the anolyte within a prescribed range. The electrolyte concentration controllers 37 and 38 may include a sensor that detects the electrolyte concentrations of the catholyte and the anolyte, an electrolyte supply device that supplies fresh catholyte and anolyte at a prescribed concentration, and a drainage device that discharges a portion of circulating catholyte and anolyte.

Further, a gas circulation flow rate adjuster 34 that discharges a portion of a gas circulating inside the gas circulation passage 26 is provided in the gas circulation passage 26. An outlet of the gas circulation flow rate adjuster 34 is connected to a first gas passage 39. A gas discharge passage of the separator 35 is connected to the first gas passage 39. The gas circulation flow rate adjuster 34 adjusts a flow rate and a pressure of a gas circulating through the gas circulation passage 26 and the cathode gas chamber 11 by discharging the gas to the first gas passage 39. A gas pressure in the cathode gas chamber 11 is maintained by the gas circulation flow rate adjuster 34 so as to be higher by a prescribed value than a liquid pressure in the catholyte chamber 12. Accordingly, the catholyte in the catholyte chamber 12 is inhibited from passing through the cathode 16 and flowing into the cathode gas chamber 11. A portion of the gas in the cathode gas chamber 11 passes through the cathode 16, and flows into the catholyte chamber 12. It is preferable that the amount of gas flowing from the cathode gas chamber 11 into the catholyte chamber 12 is small.

Carbon dioxide in the cathode gas chamber 11 diffuses inside the gas diffusion layer 21 of the cathode 16 and is reduced in the microporous layer 22, and thus a first product is acquired. The first product contains ethylene as a main product and a by-product such as methane, hydrogen, carbon monoxide, and formic acid. A large portion of the first product is generated at the cathode 16 on the side of the cathode gas chamber 11. A portion of the first product is generated at the cathode 16 on the side of the catholyte chamber 12. The first product in the catholyte chamber 12 is mixed with unreacted carbon dioxide that flows into the catholyte chamber 12. Similarly, the first product in the cathode gas chamber 11 is mixed with unreacted carbon dioxide.

Among the components of the first product generated at the cathode 16 on the side of the catholyte chamber 12, ethylene, methane, and by-produced hydrogen and carbon monoxide are gases, and are separated from the catholyte together with unreacted carbon dioxide by the separator 35 of the catholyte circulation passage 29, and then flow into the first gas passage 39. The first gas passage 39 may be provided with a separator that separates ethylene from the first product. The separator may be configured by combining a distillation device, an extraction device, and an adsorption device.

Among the components of the first product generated at the cathode 16 on the side of the cathode gas chamber 11, ethylene, methane, and by-produced hydrogen and carbon monoxide circulate through the gas circulation passage 26 together with unreacted carbon dioxide, and are discharged from the gas circulation flow rate adjuster 34 into the first gas passage 39. The first product, which includes unreacted carbon dioxide as well as ethylene, methane, and by-produced hydrogen and carbon monoxide generated at the cathode 16 on the side of the catholyte chamber 12, flows from the separator 35 and the gas circulation flow rate adjuster 34 into the first gas passage 39.

At the anode 18, water and hydroxide ions in the anolyte are oxidized, and thus gaseous oxygen is generated. Oxygen is separated from the anolyte by the separator 36 of the anolyte circulation passage 33. At the anode 18, water and hydroxide ions in the anolyte are oxidized, and thus oxygen is generated. Oxygen is a gas, and is separated from the anolyte by the separator 36 of the anolyte circulation passage 33 and flows into a second gas passage 40.

In the electrolytic reduction process 2, potentials of the cathode 16 and the catalyst carried by the cathode 16 may be set such that Faraday efficiency for producing ethylene at the cathode 16 is 30% or more, preferably 50% or more. Faraday efficiency is defined as a ratio of the current that contributes to the production of each product to the total current that flows through the electrolytic cell 14. In the electrolytic reduction process 2, the catalyst carried by the cathode 16 may be selected such that the selectivity for producing ethylene at the cathode 16 is 30% or more.

The ethylene produced in the electrolytic reduction process 2 is supplied from the first gas passage 39 to the butene producing process 3 via a first line 41. Further, the oxygen produced by the electrolytic reduction process 2 is supplied from the second gas passage 40 to the mixing process 4 via a second line 42.

In the butene producing process 3, ethylene produced in the electrolytic reduction process 2 is dimerized, and thus butene is produced.

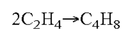

$$2C_2H_4 \rightarrow C_4H_8$$

In the butene producing process 3, butene is produced, and a main product thereof is n-butene. As shown in FIG. 2, the butene producing process 3 includes a dimerization reactor 44 and a first separator 45.

The dimerization reactor 44 may be, for example, a fixed bed flow reactor filled with an ethylene dimerization catalyst. The ethylene dimerization catalyst contains nickel, alumina, and silica. The ethylene dimerization catalyst may be, for example, a catalyst in which alumina and nickel are carried by a silica carrier, or a catalyst in which nickel is carried by a silica carrier containing alumina. The nickel content of the ethylene dimerization catalyst is 0.0001% to 1% by weight, preferably 0.0001% to 0.5% by weight, more preferably 0.0001% to 0.05% by weight.

The carrier preferably has a high specific surface area and a high pore volume. The specific surface area of the carrier is preferably 200 $m^2/g$ to 1200 $m^2/g$, and the pore volume of the carrier is preferably 0.4 cc/g to 2 cc/g. The silica carrier may be made of amorphous silica or mesoporous silica. The carrier containing silica and alumina may be made of Y-type zeolite, X-type zeolite, mordenite, beta-type zeolite, L-type zeolite, or MFI-type zeolite.

In the dimerization reactor 44, a reaction temperature of a dimerization reaction of ethylene is set to 150° C. to 400° C., preferably 200° C. to 350° C. In a case where the reaction temperature is lower than 150° C., the activity of the catalyst is lowered. In a case where the reaction temperature is higher than 400° C., branched olefin rapidly increases, nickel tends to aggregate on the catalyst, and coke tends to be by-produced. Accordingly, the catalyst may be deteriorated. A reaction pressure of dimerization of ethylene is preferably 0.1 MPa to 50 MPa. In a case where the reaction pressure is higher than 50 MPa, a by-product tends to be produced. In a case where the reaction pressure is lower than 0.1 MPa, the activity of the catalytic is lowered. The feeding velocity (weight hourly space velocity: WHSV) of ethylene per unit weight of the catalyst may be 0.1 $h^{-1}$ to 50 $h^{-1}$, preferably 0.5 $h^{-1}$ to 40 $h^{-1}$, and more preferably 0.5 $h^{-1}$ to 30 $h^{-1}$. In a case where the feeding velocity of ethylene is less than 0.1 $h^{-1}$, the productivity is lowered. Further, the selectivity of a dimer and a trimer is lowered as successive reactions of oligomerization progress. In a case where the feeding velocity of ethylene is greater than 40 $h^{-1}$, a conversion rate of ethylene is lowered.

N-butene, which includes 1-butene, cis-2-butene, and trans-2-butene, is produced as a main product by the dimerization reaction of ethylene. Further, hexene such as 1-hexene, 2-hexene, and 3-hexene may be produced as a by-product.

The first separator 45 separates n-butene from unreacted ethylene and a reaction product acquired by the dimerization of ethylene in the dimerization reactor 44.
The first separator 45 is connected to the dimerization reactor 44 via a third line 47. The first separator 45 may be configured by combining a known distillation device, extraction device, and adsorption device. Further, the first separator 45 may separate unreacted ethylene from the reaction product, and return unreacted ethylene to the dimerization reactor 44 via a return line 48. Hydrocarbon such as hexene separated by the first separator 45 may be transmitted to an after-mentioned oxygen combustion device 60 and used as fuel.

In the mixing process 4, oxygen produced in the electrolytic reduction process 2, butene produced in the butene producing process 3, and air are mixed, and thus a mixed gas is prepared. The mixing process 4 includes a gas mixer 51. The gas mixer 51 is supplied with n-butene from the first separator 45 of the butene producing process 3 via a fourth line 52, with air via an air line 53, with oxygen from the separator 36 of the electrolytic reduction process 2 via the second line 42, and with recycled gas from the carbon dioxide separating process 8 via a sixth line 55. The recycled gas mainly contains nitrogen and oxygen. Air, oxygen from the electrolytic reduction process 2, and the recycled gas are used to adjust an oxygen concentration in an after-mentioned oxidative dehydrogenation reactor 67. The mixed gas is prepared such that a molar ratio of oxygen:n-butene is kept in the range of 1:0.5 to 1:3, preferably in the range of 1:0.8 to 1:2.

The air line 53 is provided with a first flow rate control valve 57 that controls a flow rate of air supplied to the gas mixer 51. The second line 42 is provided with a second flow rate control valve 58 that controls a flow rate of oxygen supplied to the gas mixer 51. The second flow rate control valve 58 is connected via a seventh line 59 to the oxygen combustion device 60 such as a boiler that uses oxygen. Thermal energy generated in the oxygen combustion device 60 may be recovered and used to heat a gas flowing out of the gas mixer 51. Further, carbon dioxide produced by combustion in the oxygen combustion device 60 may be recovered and used as a portion of a raw material in the electrolytic reduction process 2.

The gas mixer 51 supplies the mixed gas containing ethylene, oxygen, air, and the recycled gas to the butadiene producing process 5 via an eighth line 61. An outlet of the gas mixer 51 or the eighth line 61 is provided with a first gas flowmeter 63 that measures a flow rate of the mixed gas, and an oxygen concentration meter 64 that measures an oxygen concentration of the mixed gas. Further, a pressure pump 65 that pressurizes the mixed gas and a furnace 66 that preheats the mixed gas are provided on the eighth line 61. The furnace 66 may be supplied with oxygen from the second line 42 or the seventh line 59.

In the butadiene producing process 5, the mixed gas is heated and butene is oxidatively dehydrogenated, and thus butadiene is produced.

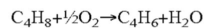

$$C_4H_8+½O_2 \rightarrow C_4H_6+H_2O$$

The butadiene producing process 5 includes the oxidative dehydrogenation reactor 67. The oxidative dehydrogenation reactor 67 may be any reactor such as a fixed bed reactor, an ebullient bed reactor, and a moving bed reactor. The oxidative dehydrogenation reactor 67 is filled with an oxidative dehydrogenation catalyst. The oxidative dehydrogenation catalyst may be a composite metal oxide catalyst containing molybdenum and bismuth, an iron oxide catalyst, a vanadium oxide catalyst, and the like. The oxidative dehydrogenation catalyst preferably contains iron and cobalt in addition to molybdenum and bismuth. The oxidative dehydrogenation catalyst may contain silica in addition to composite metal oxide.

In the oxidative dehydrogenation reactor 67, an oxidative dehydrogenation reaction is carried out at 300° C. to 600° C., preferably 300° C. to 500° C., more preferably 320° C. to 460° C. Further, the oxidative dehydrogenation reaction is carried out at 0 MPa to 2 MPa, preferably 0 MPa to 0.5 MPa. Further, a feeding velocity of n-butene per unit weight of the catalyst may be 0.1 $h^{-1}$ to 10 $h^{-1}$, more preferably 0.2 $h^{-1}$ to 5 $h^{-1}$. Butadiene as a main product is produced from n-butene by the oxidative dehydrogenation reaction. Further, carbon dioxide as a by-product is produced by complete combustion of n-butene.

An outlet of the oxidative dehydrogenation reactor 67 is connected to the butadiene separating process 7 via a ninth line 69. From the outlet of the oxidative dehydrogenation reactor 67, a gas composition containing butadiene, carbon dioxide, and unreacted mixed gas flows out. The ninth line 69 is provided with a heat exchanger 71 that constitutes the heat exchanging process 6. The gas composition passing through the ninth line 69 is cooled in the heat exchanger 71.

The gas composition is supplied to the butadiene separating process 7 via the ninth line 69, and butadiene is separated from the gas composition in the butadiene separating process 7. The butadiene separating process 7 includes a second separator 72. The second separator 72 may, for example, liquefy butadiene by cooling the gas composition, and separate liquid butadiene from the gas composition by gas-liquid separation.

The gas composition from which butadiene is separated in the butadiene separating process 7 mainly contains nitrogen, carbon dioxide, and oxygen. The gas composition from which butadiene is separated is supplied to the carbon dioxide separating process 8 via a tenth line 74, and carbon dioxide is separated from the gas composition in the carbon dioxide separating process 8. The carbon dioxide separating process 8 may include a third separator 75 that works by using a known process such as a chemisorption process such as a Benfield process and an MDEA (methyldiethanolamine) process, a physical adsorption process such as a Selexol process and a Rectisol process, a membrane separation process, a PSA process (pressure swing adsorption process), a PTSA process (pressure temperature swing adsorption process), an electrochemical separation process that uses quinone, and the like. Carbon dioxide separated from the gas composition and adsorbed by various adsorbents is separated from the adsorbents by a regeneration process, and turns into a gaseous state with a high concentration.

Carbon dioxide separated in the carbon dioxide separating process 8 is supplied from the third separator 75 to the cathode gas chamber 11 of the electrolytic reduction process 2 via an eleventh line 76. Accordingly, the carbon dioxide by-produced in the butadiene producing process 5 is used as a portion of a raw material in the electrolytic reduction process 2. Further, the eleventh line 76 is connected to a carbon dioxide line 77 that supplies a carbon dioxide gas to the eleventh line 76. The carbon dioxide line 77 is provided with a third flow rate control valve 78. The eleventh line 76 is provided with a carbon dioxide concentration meter 79 that measures a concentration of carbon dioxide passing through the eleventh line 76. Further, the eleventh line 76 is provided with a second gas flowmeter 80 that measures a flow rate of carbon dioxide passing through the eleventh line 76.

The gas composition from which carbon dioxide is separated mainly contains nitrogen and oxygen, and is returned as the recycled gas to the gas mixer 51 of the mixing process 4 via the sixth line 55. The sixth line 55 passes through the heat exchanger 71 of the heat exchanging process 6, and the recycled gas exchanges heat in the heat exchanger 71 with the gas composition passing through the ninth line 69. Accordingly, at an outlet of the heat exchanger 71, the temperature of the recycled gas passing through the sixth line 55 increases, while the temperature of the gas composition passing through the ninth line 69 decreases.

A controller 85 controls the first flow rate control valve 57 and the second flow rate control valve 58 based on signals from the first gas flowmeter 63 and the oxygen concentration meter 64. The controller 85 may increase, based on the signal from the first gas flowmeter 63, the opening degree of the first flow rate control valve 57 as the flow rate of the mixed gas decreases. Accordingly, the amount of air supplied to the gas mixer 51 increases, and thus the flow rate of the mixed gas increases. Further, the controller 85 may adjust, based on the signal from the oxygen concentration meter 64, the opening degree of the second flow rate control valve 58 and increase the flow rate of oxygen flowing from the second flow rate control valve 58 to the gas mixer 51 as the oxygen concentration of the mixed gas decreases. Accordingly, the oxygen concentration of the mixed gas can be maintained within an appropriate range.

Further, the controller 85 may control the potential of the DC power supply 19 based on signals from the carbon dioxide concentration meter 79 and the second gas flowmeter 80. Accordingly, the efficiency of the electrolytic reduction is improved. Further, the controller 85 controls the third flow rate control valve 78 based on the signals from the carbon dioxide concentration meter 79 and the second gas flowmeter 80, and adjusts the amount of carbon dioxide supplied to the carbon dioxide separating process 8.

The effect of the above embodiment will be described. The butadiene manufacturing system 1 and the manufacturing method of butadiene can produce ethylene as a raw material of butene and oxygen required for oxidative dehydrogenation by using carbon dioxide that is generated when butadiene is produced by oxidative dehydrogenation. Thus, the emission of carbon dioxide as a greenhouse gas generated during the production of butadiene can be reduced. Further, the cost of a raw material can be reduced in the manufacturing method of butadiene.

Carbon dioxide generated in the butadiene producing process 5 is concentrated through the heat exchanging process 6, the butadiene separating process 7, and the carbon dioxide separating process 8, and is supplied to the electrolytic reduction process 2. Accordingly, the efficiency of the electrolytic reduction can be improved. The gas composition from which the carbon dioxide is separated in the carbon dioxide separating process 8 is mixed with the mixed gas in the mixing process 4 after exchanging heat in the heat exchanging process 6 with the gas composition flowing out in the butadiene producing process 5 and containing the butadiene and the carbon dioxide. Accordingly, the energy consumption for heating the oxidative dehydrogenation reactor 67 of the butadiene producing process 5 can be reduced. Further, the gas composition flowing out in the butadiene producing process 5 and containing butadiene and carbon dioxide can be cooled, and thus energy efficiency can be improved.

Figure 4:
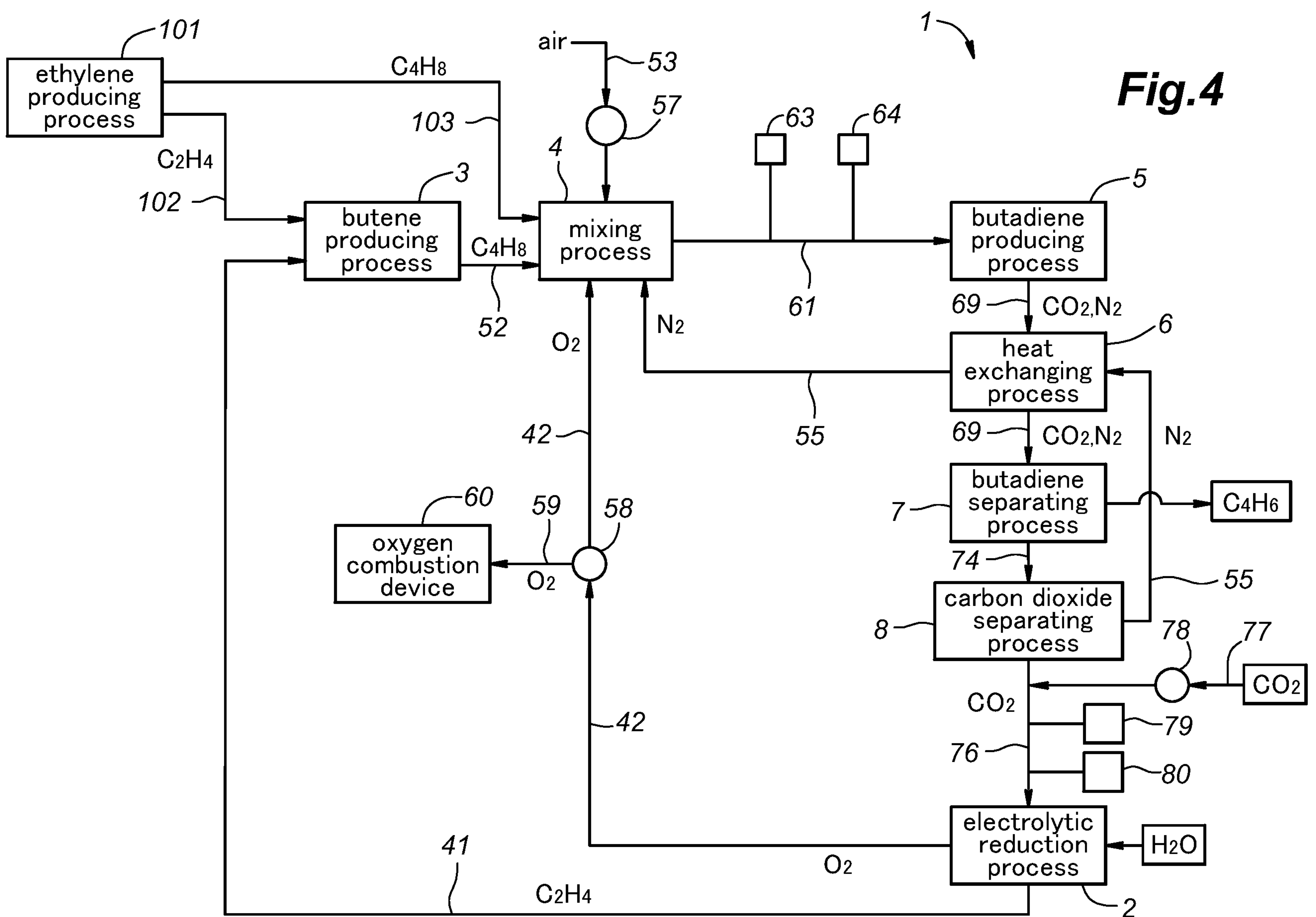
FIG. 4 is an explanatory diagram showing a butadiene manufacturing system according to a modified embodiment.

As shown in FIG. 4, the butadiene manufacturing system 1 may further include an ethylene producing process 101 that produces ethylene from ethane or naphtha as a raw material. The ethylene producing process 101 may produce ethylene by ethane cracking of ethane as a raw material or naphtha cracking of naphtha as a raw material. A portion of ethylene produced in the ethylene producing process 101 may be supplied to the butene producing process 3 via a twelfth line 102, and used as a portion of a raw material in the butene producing process 3.

Further, butene by-produced in the ethylene producing process 101 may be supplied to the mixing process 4 via a thirteenth line 103 and used in the butadiene producing process 5. In this case, the twelfth line 102 may be omitted. Further, in a case where the ethylene producing process 101 is provided, the carbon dioxide line 77 may be omitted since the amount of ethylene that needs to be produced in the electrolytic reduction process 2 is reduced.

As an example, in the three-chamber electrolytic cell 14 composed of the cathode gas chamber 11, the catholyte chamber 12, and the anolyte chamber 13, the cathode 16 was formed of a gas diffusion electrode that carries a copper-zinc composite catalyst, and the anode 18 was formed of a Pt mesh. The electricity was applied at 265 mA/cm 2 for 6 hours while a potassium hydrogen carbonate aqueous solution of 1M (1 mol/L) was supplied at 1 mL/min to each of the catholyte chamber 12 and the anolyte chamber 13, and carbon dioxide was supplied at 100 mL/min to the cathode gas chamber 11. Analysis of the products in the gas showed that the cathode 16 produced 37% ethylene, 1% methane, and 25% hydrogen in Faraday efficiency, and the anode 18 produced a gas with 99% oxygen in the Faraday efficiency.

In the butadiene manufacturing system shown in FIG. 4, a process calculation was performed in a case where 100 kg/hr of butadiene was produced. In a case where 100 kg/hr of butadiene was produced in the butadiene producing process 5, 12 kg/hr of ethylene was supplied from the electrolytic reduction process 2 to the butene producing process 3, 250 kg/hr of ethylene was supplied from the ethylene producing process 101 to the butene producing process 3, 205 kg/hr of butene was supplied from the butene producing process 3 to the mixing process 4, air containing 10 kg/hr of oxygen was supplied from the air line 53 to the mixing process 4, 56 kg/hr of oxygen was supplied from the electrolytic reduction process 2 to the mixing process 4, and 50 kg/hr of carbon dioxide was supplied from the butadiene producing process 5 to the electrolytic reduction process 2. That is, 50 kg/hr of carbon dioxide was produced in the butadiene producing process 5, 12 kg/hr of ethylene and 56 kg/hr of oxygen were produced from this carbon dioxide as a raw material in the electrolytic reduction process 2. In this case, the selectivity of ethylene in the electrolytic reduction process 2 was set at 80%.

Concrete embodiments of the present invention have been described in the foregoing, but the present invention should not be limited by the foregoing embodiments and various modifications and alterations are possible within the scope of the present invention.

GLOSSARY OF TERMS

1: butadiene manufacturing system
2: electrolytic reduction process
5: butadiene producing process
6: heat exchanging process
7: butadiene separating process
8: carbon dioxide separating process
10: electrolytic reductor
44: dimerization reactor
51: gas mixer
57: first flow rate control valve
58: second flow rate control valve
61: oxygen combustion device
63: first gas flowmeter
64: oxygen concentration meter
67: oxidative dehydrogenation reactor
71: heat exchanger
72: second separator
85: controller
101: ethylene producing process
102: twelve line
103: thirteenth line

What is claimed is:

1. A manufacturing method of butadiene, comprising:

an electrolytic reduction process that produces ethylene and oxygen from carbon dioxide and water as a raw material by electrolytic reduction;

a butene producing process that produces butene by dimerizing the ethylene produced in the electrolytic reduction process;

a mixing process that prepares a mixed gas by mixing the oxygen produced in the electrolytic reduction process, the butene produced in the butene producing process, and air; and a butadiene producing process that produces butadiene by heating the mixed gas and oxidatively dehydrogenating the butene, wherein carbon dioxide by-produced in the butadiene producing process is used as a portion of the raw material in the electrolytic reduction process.

2. The manufacturing method of butadiene according to claim 1, comprising:

a heat exchanging process that cools a gas composition flowing out in the butadiene producing process and containing the butadiene and the carbon dioxide;

a butadiene separating process that separates the butadiene from the gas composition cooled in the heat exchanging process; and a carbon dioxide separating process that separates the carbon dioxide from the gas composition from which the butadiene is separated in the butadiene separating process, wherein the carbon dioxide separated in the carbon dioxide separating process is used as the portion of the raw material in the electrolytic reduction process.

3. The manufacturing method of butadiene according to claim 2, wherein in the heat exchanging process, the gas composition flowing out in the butadiene producing process and containing the butadiene and the carbon dioxide is cooled by exchanging heat with the gas composition from which the carbon dioxide is separated in the carbon dioxide separating process.

4. The manufacturing method of butadiene according to claim 3, wherein the gas composition from which the carbon dioxide is separated in the carbon dioxide separating process is mixed with the mixed gas in the mixing process after exchanging heat in the heat exchanging process with the gas composition flowing out in the butadiene producing process and containing the butadiene and the carbon dioxide.

5. The manufacturing method of butadiene according to claim 1, comprising:

measuring an oxygen concentration and a flow rate of the mixed gas in the mixing process; and controlling a flow rate of the oxygen supplied from the electrolytic reduction process to the mixing process based on the oxygen concentration and the flow rate of the mixed gas.

6. The manufacturing method of butadiene according to claim 1, comprising:

measuring a flow rate of the carbon dioxide supplied from the butadiene producing process to the electrolytic reduction process; and controlling a potential of the electrolytic reduction in the electrolytic reduction process based on the flow rate of the carbon dioxide.

7. The manufacturing method of butadiene according to claim 1, further comprising an ethylene producing process that produces ethylene from ethane or naphtha as a raw material, wherein the ethylene produced in the ethylene producing process is used as a portion of a raw material in the butene producing process.

8. The manufacturing method of butadiene according to claim 7, wherein butene by-produced in the ethylene producing process is used in the butadiene producing process.

* * * * *